United States Patent
Adhikari

(10) Patent No.: US 12,217,835 B2
(45) Date of Patent: Feb. 4, 2025

(54) SYSTEMS AND METHODS FOR HASHING-BASED ASSESSMENT OF ELECTRONIC CLINICAL TRIAL OUTCOMES

(71) Applicant: eResearchTechnology, Inc., Philadelphia, PA (US)

(72) Inventor: Udit Adhikari, Billerica, MA (US)

(73) Assignee: eResearchTechnology, Inc., Philadelphia, PA (US)

( * ) Notice: Subject to any disclaimer, the term of this patent is extended or adjusted under 35 U.S.C. 154(b) by 442 days.

(21) Appl. No.: 16/830,903

(22) Filed: Mar. 26, 2020

(65) Prior Publication Data

US 2021/0295956 A1    Sep. 23, 2021

Related U.S. Application Data

(60) Provisional application No. 62/991,279, filed on Mar. 18, 2020.

(51) Int. Cl.
| | |
|---|---|
| *G06F 11/36* | (2006.01) |
| *G06F 16/18* | (2019.01) |
| *G06F 16/901* | (2019.01) |
| *G16H 10/20* | (2018.01) |
| *H04L 9/32* | (2006.01) |

(52) U.S. Cl.
CPC ......... *G16H 10/20* (2018.01); *G06F 11/3688* (2013.01); *G06F 16/1873* (2019.01); *G06F 16/9027* (2019.01); *H04L 9/3239* (2013.01); *H04L 9/3242* (2013.01)

(58) Field of Classification Search
CPC ......... G06F 11/36; G06F 16/18; G06F 16/901
See application file for complete search history.

(56) References Cited

U.S. PATENT DOCUMENTS

| | | |
|---|---|---|
| 6,879,970 B2 | 4/2005 | Shiffman et al. |
| 7,415,447 B2 | 8/2008 | Shiffman et al. |
| 7,873,589 B2 | 1/2011 | Shiffman et al. |
| 8,065,180 B2 | 11/2011 | Hufford et al. |
| 8,145,519 B2 | 3/2012 | Hufford et al. |
| 8,273,019 B2 | 9/2012 | Crowley et al. |
| 8,380,531 B2 | 2/2013 | Paty et al. |
| 8,433,605 B2 | 4/2013 | Hufford et al. |

(Continued)

*Primary Examiner* — Maher N Algibhah
(74) *Attorney, Agent, or Firm* — BUCHANAN, INGERSOLL & ROONEY PC

(57) ABSTRACT

The present disclosure is related to systems and methods for hashing-based assessment of electronic clinical trial outcomes. Such systems and methods may advantageously enable secure, rapid, efficient, and cost-effective reuse of pre-built eCOA assessments for clinical trials. In an aspect, the present disclosure provides a computer-implemented method for validation of an electronic clinical trial outcome assessment (eCOA), comprising: (a) obtaining an assessment of an eCOA, the assessment comprising a plurality of files generated by performing a first validation of the eCOA; (b) obtaining a first hash value associated with the assessment of the eCOA, the first hash value generated by hashing the plurality of files of the assessment of the eCOA; (c) hashing the plurality of files of the assessment of the eCOA to generate a second hash value; and (d) validating the eCOA when the second hash value is equal to the first hash value.

13 Claims, 6 Drawing Sheets

(56) References Cited

U.S. PATENT DOCUMENTS

| | | |
|---|---|---|
| 8,533,029 B2 | 9/2013 | Hufford et al. |
| 9,075,900 B2 | 7/2015 | Wilson et al. |
| 9,129,215 B2 | 9/2015 | Shiffman et al. |
| 9,414,776 B2 | 8/2016 | Sillay et al. |
| 9,483,618 B2 | 11/2016 | Brincat et al. |
| 9,881,062 B2 | 1/2018 | Shiffman et al. |
| 10,049,368 B2 | 8/2018 | Hansen et al. |
| 10,276,054 B2 | 4/2019 | Eger et al. |
| 10,897,361 B1* | 1/2021 | Miller ................... H04L 9/0894 |
| 2006/0259783 A1* | 11/2006 | Work ..................... G16H 10/20 |
| | | 713/189 |
| 2007/0106754 A1 | 5/2007 | Moore |
| 2011/0119076 A1 | 5/2011 | Dhoble |
| 2011/0283110 A1* | 11/2011 | Dapkus ................. H04L 9/3234 |
| | | 713/182 |
| 2014/0222349 A1* | 8/2014 | Higgins ................ G16B 20/00 |
| | | 702/19 |
| 2016/0085976 A1* | 3/2016 | Schiffman ............ G06F 21/606 |
| | | 726/30 |
| 2016/0132311 A1* | 5/2016 | Beckman ............ G06F 9/45529 |
| | | 717/177 |
| 2019/0013948 A1* | 1/2019 | Mercuri ................. G06F 9/451 |
| 2019/0052467 A1* | 2/2019 | Bettger ................ G06F 21/602 |
| 2019/0213117 A1* | 7/2019 | Li ....................... G06F 11/3684 |
| 2019/0222560 A1 | 7/2019 | Ford et al. |
| 2020/0364373 A1* | 11/2020 | Huang ................. H04L 9/3239 |
| 2020/0372980 A1* | 11/2020 | de Vries ................ G16H 40/20 |
| 2021/0109919 A1* | 4/2021 | Raj ........................ G06F 21/64 |

* cited by examiner

Running (hash) task

```
trial\handheld\diaries\Lib_ACQ-6\changeLog.txt
trial\handheld\diaries\Lib_ACQ-6\diary\ACQ6.js
trial\handheld\diaries\Lib_ACQ-6\index.js
trial\handheld\diaries\Lib_ACQ-6\less\ACQ-6.less
trial\handheld\diaries\Lib_ACQ-6\nls\en-US\studyStrings.ACQ6.en_US.json
```

The hashing file was successfully written.

FIG. 5

```
Hashing performed at : Sat Nov 16 2019 11:17:17 GMT-0500 (Eastern Standard Time) for modality : handheld Library Diary : XLQ-6 ---> hash : 47b3499a1df33670994565b9730ecaf1c Library Diary : SQLQ312 ---> hash : 9a088a5417991811633ea8389d0062c5

Library Diary : ECRIC-QLQ-C30 ---> hash : cc9b54d31a3efb133bahb018b0a8f547

Library Diary : fact ---> hash : 3434e6896Ga1669fb6fcGec831d35a6a
```

FIG. 6

SYSTEMS AND METHODS FOR HASHING-BASED ASSESSMENT OF ELECTRONIC CLINICAL TRIAL OUTCOMES

CROSS-REFERENCE

This application claims the benefit of U.S. Patent Application No. 62/991,279, filed Mar. 18, 2020, which is entirely incorporated by reference herein.

BACKGROUND

The use of electronic clinical trial outcomes assessments (eCOAs) can yield numerous advantages for clinical trial building compared to paper-based outcomes assessment approaches, including higher data quality and higher compliance. However, development and testing of eCOAs typically costs a lot of time and resources during clinical trial building.

SUMMARY

The present disclosure is related to systems and methods for hashing-based assessment of electronic clinical trial outcomes. Such systems and methods may advantageously enable secure, rapid, efficient, and cost-effective reuse of pre-built eCOA assessments for clinical trials.

In an aspect, the present disclosure can provide for a computer-implemented method for validation of an electronic clinical trial outcome assessment (eCOA), comprising: (a) obtaining an assessment of an eCOA, the assessment comprising a plurality of files generated by performing a first validation of the eCOA; (b) obtaining a first hash value associated with the assessment of the eCOA, the first hash value generated by hashing the plurality of files of the assessment of the eCOA; (c) hashing the plurality of files of the assessment of the eCOA to generate a second hash value; and (d) validating the eCOA when the second hash value is equal to the first hash value.

In some embodiments, (c) can comprise sequentially hashing the plurality of files of the assessment of the eCOA. In some embodiments, (c) can comprise hashing the plurality of files of the assessment of the eCOA in a pre-determined order. In some embodiments, the plurality of files can comprise one or more folders. In some embodiments, the pre-determined order can correspond to a tree traversal technique. In some embodiments, the tree traversal technique can comprise a recursive tree traversal technique. In some embodiments, the tree traversal technique can comprise a depth-first search (DFS) or a breadth-first search (BFS). In some embodiments, the tree traversal technique can comprise a depth-first search (DFS). In some embodiments, the tree traversal technique can comprise a breadth-first search (BFS).

In some embodiments, (c) can comprise applying a hash algorithm to the plurality of files of the assessment of the eCOA. In some embodiments, the assessment of the eCOA can be a standardized assessment. In some embodiments, the hash algorithm can be a deterministic algorithm. In some embodiments, the hash algorithm can be a deterministic algorithm based on an order in which the plurality of files of the assessment of the eCOA is hashed. In some embodiments, the hash algorithm can be a message authentication code (MAC) algorithm. In some embodiments, the MAC algorithm can be a Keyed-Hash MAC (HMAC) algorithm. In some embodiments, the hash algorithm can be selected from Message Digest 5 (MD5), Secure Hash Algorithm (SHA)-0, Secure Hash Algorithm (SHA)-1, Secure Hash Algorithm (SHA)-2, Secure Hash Algorithm (SHA)-224, Secure Hash Algorithm (SHA)-256, Secure Hash Algorithm (SHA)-384, Secure Hash Algorithm (SHA)-512, Microsoft LAN Manager (LANMAN), Microsoft NT LAN Manager (NTLM), NTLMv2 or a combination thereof. In some embodiments, the has algorithm can be MD5. In some embodiments, the same hash algorithm can be used to generate the first hash value and the second hash value. In some embodiments, the first hash value and the second hash value can be generated by hashing the plurality of files of the assessment of the eCOA in the same order. In some embodiments, the first hash value and the second hash value can be generated by hashing the plurality of files of the assessment of the eCOA in a different order.

In some embodiments, (a) can comprise retrieving the assessment of the eCOA from a database. In some embodiments, the method can further comprise retrieving the assessment of the eCOA from the database over a computer network. In some embodiments, the computer network can be a cloud-based network.

In some embodiments, the method can further comprise, prior to (a), generating the assessment by performing the first validation of the eCOA. In some embodiments, the method can further comprise storing the assessment in a database. In some embodiments, the database can be a versioning system. In some embodiments, the method can further comprise, prior to (b), generating the first hash value by hashing the plurality of files of the assessment of the eCOA. In some embodiments, the method can further comprise storing the first hash value in a database. In some embodiments, the first validation of the eCOA can be performed by regression testing. In some embodiments, the regression testing can comprise a full extensive regression testing.

In some embodiments, the method can further comprise generating an indication that the eCOA has been validated. In some embodiments, the method can further comprise providing the indication that the eCOA has been validated to a user. In some embodiments, the method can further comprise, responsive to the indication that the eCOA has been validated, using the eCOA without performing further validation of the eCOA. In some embodiments, the method can further comprise, responsive to the indication that the eCOA has been validated, using the eCOA without performing further development of the eCOA. In some embodiments, the method can further comprise using the eCOA to construct a clinical trial.

In some embodiments, a standard assessment can be initially developed and fully tested (e.g., by regression testing), and a hash value of the standard assessment can be obtained and stored in a database or repository. In some embodiments, when a clinical study or a clinical trial is performed with a requirement to use a particular standard assessment, the standard assessment and its associated hash value can be retrieved from the database or repository. In some embodiments, the standard assessment can be hashed to produce a second hash value, which can be compared to the initial hash value. In some embodiments, upon validation of the standard assessment by confirming that the hash values are identical, no further testing is performed on the standard assessment. In some embodiments, upon determining that the hash values are not identical, a full regression testing may be performed on the standard assessment, or the standard assessment may be retrieved from another source (e.g., a backup database or repository). In some embodiments a first hash algorithm is used on the standard assessment to generate a first hash value and the same first hash algorithm is used to generate a second has value In some embodiments, the method can further comprise generating an indication that the eCOA is not valid when the second hash value is not equal to the first hash value. In some embodiments, the method can further comprise providing the indication that the eCOA is not valid to a user. In some embodiments, the method can further comprise, responsive to the indication that the eCOA is not valid, obtaining a second assessment of the eCOA by performing a second validation of the eCOA. In some embodiments, the method can further comprise, responsive to the indication that the eCOA is not valid, obtaining a second eCOA and validating the second eCOA. In some embodiments, validating the second eCOA can comprise: obtaining a second assessment of the second eCOA, the second assessment comprising a second plurality of files generated by performing a second validation of the second eCOA; obtaining a third hash value associated with the second assessment of the second eCOA, the third hash value generated by hashing a second plurality of files of the second assessment of the second eCOA; hashing the second plurality of files of the second assessment of the second eCOA to generate a fourth hash value; and validating the second eCOA when the fourth hash value is equal to the third hash value. In some embodiments, the method can further comprise permitting use of the eCOA only upon validation of the eCOA when the second hash value is equal to the first hash value.

In some embodiments, performing the first validation of the eCOA can comprise collecting endpoint data of a plurality of patients. In some embodiments, the first validation of the eCOA can be performed using an electronic device. In some embodiments, the electronic device can comprise a mobile device selected from a smart phone, a tablet computer, a laptop computer, and a smart watch. In some embodiments, the electronic device can have internet or WiFi connectivity. In some embodiments, the electronic device can be a portable electronic device. In some embodiments, performing the first validation of the eCOA can comprise ensuring one or more of efficiency, accessibility, and equivalency of the eCOA.

In another aspect, the present disclosure can provide for a computer system for validation of an electronic clinical trial outcome assessment (eCOA), comprising: a database that can be configured to store (i) an assessment of an eCOA, the assessment comprising a plurality of files generated by performing a first validation of the eCOA and (ii) a first hash value associated with the assessment of the eCOA, the first hash value generated by hashing the plurality of files of the assessment of the eCOA; and one or more computer processors operatively coupled to the database, wherein the one or more computer processors can be individually or collectively programmed to: hash the plurality of files of the assessment of the eCOA to generate a second hash value; and validate the eCOA when the second hash value is equal to the first hash value.

In some embodiments, hashing the plurality of files of the assessment of the eCOA can comprise sequentially hashing the plurality of files of the assessment of the eCOA. In some embodiments, hashing the plurality of files of the assessment of the eCOA can comprise hashing the plurality of files of the assessment of the eCOA in a pre-determined order. In some embodiments, the plurality of files can comprise one or more folders. In some embodiments, the pre-determined order can correspond to a tree traversal technique. In some embodiments, the tree traversal technique can comprise a recursive tree traversal technique. In some embodiments, the tree traversal technique can comprise a depth-first search (DFS) or a breadth-first search (BFS). In some embodiments, the tree traversal technique can comprise a depth-first search (DFS). In some embodiments, the tree traversal technique can comprise a breadth-first search (BFS).

In some embodiments, hashing the plurality of files of the assessment of the eCOA can comprise applying a hash algorithm to the plurality of files of the assessment of the eCOA. In some embodiments, the assessment of the eCOA can be a standardized assessment. In some embodiments, the hash algorithm can be a deterministic algorithm. In some embodiments, the hash algorithm can be a deterministic algorithm based on an order in which the plurality of files of the assessment of the eCOA is hashed. In some embodiments, the hash algorithm can be a message authentication code (MAC) algorithm. In some embodiments, the MAC algorithm can be a Keyed-Hash MAC (HMAC) algorithm. In some embodiments, the hash algorithm can be selected from Message Digest 5 (MD5), Secure Hash Algorithm (SHA)-0, Secure Hash Algorithm (SHA)-1, Secure Hash Algorithm (SHA)-2, Secure Hash Algorithm (SHA)-224, Secure Hash Algorithm (SHA)-256, Secure Hash Algorithm (SHA)-384, Secure Hash Algorithm (SHA)-512, Microsoft LAN Manager (LANMAN), Microsoft NT LAN Manager (NTLM), NTLMv2 or a combination thereof. In some embodiments, the hash algorithm can be MD5. In some embodiments, the same hash algorithm can be used to generate the first hash value and the second hash value. In some embodiments, the first hash value and the second hash value can be generated by hashing the plurality of files of the assessment of the eCOA in the same order. In some embodiments, the first hash value and the second hash value can be generated by hashing the plurality of files of the assessment of the eCOA in a different order. In some embodiments, a first algorithm can be used to hash a standardized assessment and the same has algorithm can be used to hash an assessment in a clinical trial.

In some embodiments, the one or more computer processors can individually or collectively be programmed to further retrieve the assessment of the eCOA from a second database. In some embodiments, the one or more computer processors can individually or collectively be programmed to further retrieve the assessment of the eCOA from the second database over a computer network. In some embodiments, the computer network can be a cloud-based network.

In some embodiments, the one or more computer processors can be individually or collectively programmed to further, prior to (a), generate the assessment by performing the first validation of the eCOA. In some embodiments, the one or more computer processors can be individually or collectively programmed to further store the assessment in a database. In some embodiments, the database can be a versioning system. In some embodiments, the one or more computer processors can be individually or collectively programmed to further, prior to (b), generate the first hash value by hashing the plurality of files of the assessment of the eCOA. In some embodiments, the one or more computer processors can be individually or collectively programmed to further store the first hash value in a database. In some embodiments, the first validation of the eCOA can be performed by regression testing. In some embodiments, the regression testing can comprise a full extensive regression testing.

In some embodiments, the one or more computer processors can be individually or collectively programmed to further generate an indication that the eCOA has been validated. In some embodiments, the one or more computer processors can be individually or collectively programmed to further provide the indication that the eCOA has been validated to a user. In some embodiments, the one or more computer processors can be individually or collectively programmed to further, responsive to the indication that the eCOA has been validated, use the eCOA without performing further validation of the eCOA. In some embodiments, the one or more computer processors can be individually or collectively programmed to further, responsive to the indication that the eCOA has been validated, use the eCOA without performing further development of the eCOA. In some embodiments, the one or more computer processors can be individually or collectively programmed to further use the eCOA to construct a clinical trial.

In some embodiments, a standard assessment can be initially developed and fully tested (e.g., by regression testing), and a hash value of the standard assessment can be obtained and stored in a database or repository. In some embodiments, when a clinical study or a clinical trial is performed with a requirement to use a particular standard assessment, the standard assessment and its associated hash value are retrieved from the database or repository. In some embodiments, the standard assessment can be hashed to produce a second hash value, which can be compared to the initial hash value. In some embodiments, upon validation of the standard assessment by confirming that the hash values are identical, no further testing is performed on the standard assessment. In some embodiments, upon determining that the hash values are not identical, a full regression testing may be performed on the standard assessment, or the standard assessment may be retrieved from another source (e.g., a backup database or repository).

In some embodiments, the one or more computer processors can be individually or collectively programmed to further generate an indication that the eCOA is not valid when the second hash value is not equal to the first hash value. In some embodiments, the one or more computer processors can be individually or collectively programmed to further provide the indication that the eCOA is not valid to a user. In some embodiments, the one or more computer processors can be individually or collectively programmed to further, responsive to the indication that the eCOA is not valid, obtain a second assessment of the eCOA by performing a second validation of the eCOA. In some embodiments, the one or more computer processors can be individually or collectively programmed to further, responsive to the indication that the eCOA is not valid, obtain a second eCOA and validating the second eCOA. In some embodiments, validating the second eCOA can comprise: obtaining a second assessment of the second eCOA, the second assessment comprising a second plurality of files generated by performing a second validation of the second eCOA; obtaining a third hash value associated with the second assessment of the second eCOA, the third hash value generated by hashing a second plurality of files of the second assessment of the second eCOA; hashing the second plurality of files of the second assessment of the second eCOA to generate a fourth hash value; and validating the second eCOA when the fourth hash value is equal to the third hash value. In some embodiments, the one or more computer processors can be individually or collectively programmed to further permit use of the eCOA only upon validation of the eCOA when the second hash value is equal to the first hash value.

In some embodiments, performing the first validation of the eCOA can comprise collecting endpoint data of a plurality of patients. In some embodiments, the first validation of the eCOA is performed using an electronic device. In some embodiments, the electronic device can comprise a mobile device selected from a smart phone, a tablet computer, a laptop computer, and a smart watch. In some embodiments, the electronic device can have internet or WiFi connectivity. In some embodiments, performing the first validation of the eCOA can comprise ensuring one or more of efficiency, accessibility, and equivalency of the eCOA.

In another aspect, the present disclosure can provide a non-transitory computer-readable medium comprising machine-executable instructions which, upon execution by one or more computer processors, can perform a method for validation of an electronic clinical trial outcome assessment (eCOA), the method comprising: (a) obtaining an assessment of an eCOA, the assessment comprising a plurality of files generated by performing a first validation of the eCOA; (b) obtaining a first hash value associated with the assessment of the eCOA, the first hash value generated by hashing the plurality of files of the assessment of the eCOA; (c) hashing the plurality of files of the assessment of the eCOA to generate a second hash value; and (d) validating the eCOA when the second hash value is equal to the first hash value.

In some embodiments, (c) can comprise sequentially hashing the plurality of files of the assessment of the eCOA. In some embodiments, (c) can comprise hashing the plurality of files of the assessment of the eCOA in a pre-determined order. In some embodiments, the plurality of files can comprise one or more folders. In some embodiments, the pre-determined order can correspond to a tree traversal technique. In some embodiments, the tree traversal technique can comprise a recursive tree traversal technique. In some embodiments, the tree traversal technique can comprise a depth-first search (DFS) or a breadth-first search (BFS). In some embodiments, the tree traversal technique can comprise a depth-first search (DFS). In some embodiments, the tree traversal technique can comprise a breadth-first search (BFS).

In some embodiments, (c) can comprise applying a hash algorithm to the plurality of files of the assessment of the eCOA. In some embodiments, the assessment of the eCOA can be a standardized assessment. In some embodiments, the hash algorithm can be a deterministic algorithm. In some embodiments, the hash algorithm can be a deterministic algorithm based on an order in which the plurality of files of the assessment of the eCOA is hashed. In some embodiments, the hash algorithm can be a message authentication code (MAC) algorithm. In some embodiments, the MAC algorithm can be a Keyed-Hash MAC (HMAC) algorithm. In some embodiments, the hash algorithm can be selected from Message Digest 5 (MD5), Secure Hash Algorithm (SHA)-0, Secure Hash Algorithm (SHA)-1, Secure Hash Algorithm (SHA)-2, Secure Hash Algorithm (SHA)-224, Secure Hash Algorithm (SHA)-256, Secure Hash Algorithm (SHA)-384, Secure Hash Algorithm (SHA)-512, Microsoft LAN Manager (LANMAN), Microsoft NT LAN Manager (NTLM), NTLMv2 and a combination thereof. In some embodiments, the has algorithm can be MD5. In some embodiments, the same hash algorithm can be used to generate the first hash value and the second hash value. In some embodiments, the first hash value and the second hash value can be generated by hashing the plurality of files of the assessment of the eCOA in the same order. In some embodiments, a different hash algorithm can be used to generate the first hash value and the second hash value. In some embodiments, the first hash value and the second hash value can be generated by hashing the plurality of files of the assessment of the eCOA in a different order.

In some embodiments, (a) can comprise retrieving the assessment of the eCOA from a database. In some embodiments, the method further can comprise retrieving the assessment of the eCOA from the database over a computer network. In some embodiments, the computer network is a cloud-based network.

In some embodiments, the method further can comprise, prior to (a), generating the assessment by performing the first validation of the eCOA. In some embodiments, the method further can comprise storing the assessment in a database. In some embodiments, the database can be a versioning system. In some embodiments, the method further can comprise, prior to (b), generating the first hash value by hashing the plurality of files of the assessment of the eCOA. In some embodiments, the method further can comprise storing the first hash value in a database. In some embodiments, the first validation of the eCOA can be performed by regression testing. In some embodiments, the regression testing can comprise a full extensive regression testing.

In some embodiments, the method further can comprise generating an indication that the eCOA has been validated. In some embodiments, the method further can comprise providing the indication that the eCOA has been validated to a user. In some embodiments, the method further can comprise, responsive to the indication that the eCOA has been validated, using the eCOA without performing further validation of the eCOA. In some embodiments, the method further can comprise, responsive to the indication that the eCOA has been validated, using the eCOA without performing further development of the eCOA. In some embodiments, the method further can comprise using the eCOA to construct a clinical trial.

In some embodiments, a standard assessment can be initially developed and fully tested (e.g., by regression testing), and a hash value of the standard assessment can be obtained and stored in a database or repository. In some embodiments, when a clinical study or a clinical trial is performed with a requirement to use a particular standard assessment, the standard assessment and its associated hash value are retrieved from the database or repository. In some embodiments, the standard assessment is hashed to produce a second hash value, which is compared to the initial hash value. In some embodiments, upon validation of the standard assessment by confirming that the hash values are identical, no further testing is performed on the standard assessment. In some embodiments, upon determining that the hash values are not identical, a full regression testing may be performed on the standard assessment, or the standard assessment may be retrieved from another source (e.g., a backup database or repository).

In some embodiments, the method further can comprise generating an indication that the eCOA is not valid when the second hash value is not equal to the first hash value. In some embodiments, the method further can comprise providing the indication that the eCOA is not valid to a user. In some embodiments, the method further can comprise, responsive to the indication that the eCOA is not valid, obtaining a second assessment of the eCOA by performing a second validation of the eCOA. In some embodiments, the method further can comprise, responsive to the indication that the eCOA is not valid, obtaining a second eCOA and validating the second eCOA. In some embodiments, validating the second eCOA can comprise: obtaining a second assessment of the second eCOA, the second assessment comprising a second plurality of files generated by performing a second validation of the second eCOA; obtaining a third hash value associated with the second assessment of the second eCOA, the third hash value generated by hashing a second plurality of files of the second assessment of the second eCOA; hashing the second plurality of files of the second assessment of the second eCOA to generate a fourth hash value; and validating the second eCOA when the fourth hash value is equal to the third hash value. In some embodiments, the method further can comprise permitting use of the eCOA only upon validation of the eCOA when the second hash value is equal to the first hash value.

In some embodiments, performing the first validation of the eCOA can comprise collecting endpoint data of a plurality of patients. In some embodiments, the first validation of the eCOA can be performed using an electronic device. In some embodiments, the electronic device can comprise a mobile device selected from a smart phone, a tablet computer, a laptop computer, and a smart watch. In some embodiments, the electronic device can comprise a portable electronic device. In some embodiments, the electronic device can have internet or WiFi connectivity. In some embodiments, performing the first validation of the eCOA can comprise ensuring one or more of efficiency, accessibility, and equivalency of the eCOA.

Another aspect of the present disclosure can provide for a non-transitory computer-readable medium comprising machine executable code that, upon execution by one or more computer processors, implements any of the methods above or elsewhere herein.

Another aspect of the present disclosure can provide for a system comprising one or more computer processors and computer memory coupled thereto. The computer memory can comprise machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 5 shows an example of the order in which the files inside Lib_ACQ-6 are processed and their contents processed by the hashing algorithm, upon performing the hashing task, in accordance with disclosed embodiments.

FIG. 6 shows an example of the output of the hashing algorithm, in accordance with disclosed embodiments.

DETAILED DESCRIPTION

Figure 1:
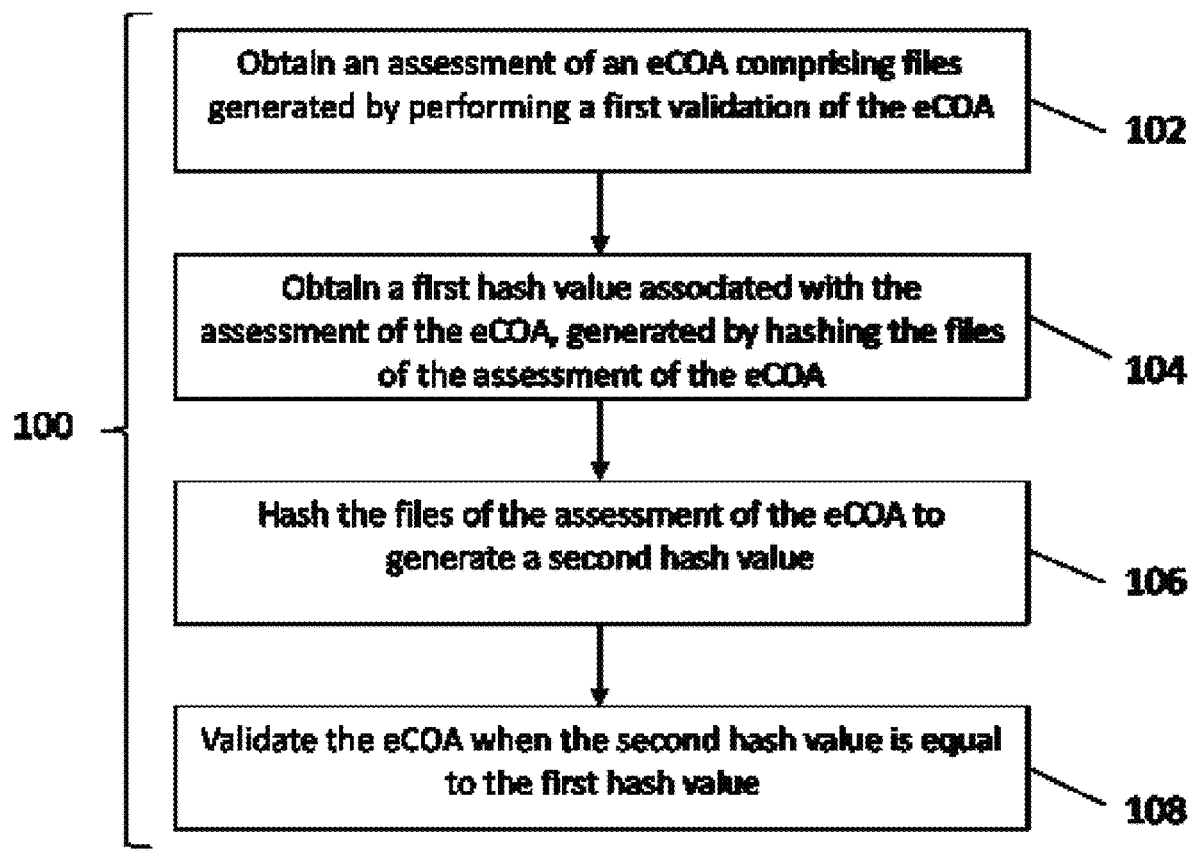
FIG. 1 shows an example of a method 100 for validation of an electronic clinical trial outcome assessment (eCOA), in accordance with disclosed embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used in the specification and claims, the singular form "a", "an" and "the" include plural references unless the context clearly dictates otherwise. For example, the term "a biological sample" includes a plurality of biological samples, including mixtures thereof.

The use of electronic clinical trial outcomes assessments (eCOAs) can yield numerous advantages for clinical trial building compared to paper-based outcomes assessment approaches, including higher data quality and higher compliance. However, development and testing of eCOAs typically costs a lot of time and resources during clinical trial building.

The present disclosure can relate to systems and methods for hashing-based assessment of electronic clinical trial outcomes. Such systems and methods may advantageously enable secure, rapid, efficient, and cost-effective reuse of pre-built eCOA assessments for clinical trials.

In an aspect, the present disclosure can provide for a computer-implemented method for validation of an electronic clinical trial outcome assessment (eCOA), comprising: (a) obtaining an assessment of an eCOA, the assessment comprising a plurality of files generated by performing a first validation of the eCOA; (b) obtaining a first hash value associated with the assessment of the eCOA, the first hash value generated by hashing the plurality of files of the assessment of the eCOA; (c) hashing the plurality of files of the assessment of the eCOA to generate a second hash value; and (d) validating the eCOA when the second hash value is equal to the first hash value.

In some embodiments, (c) can comprise sequentially hashing the plurality of files of the assessment of the eCOA. In some embodiments, (c) can comprise hashing the plurality of files of the assessment of the eCOA in a pre-determined order. In some embodiments, the plurality of files can comprise one or more folders. In some embodiments, the pre-determined order corresponds to a tree traversal technique. In some embodiments, the tree traversal technique can comprise a depth-first search (DFS) or a breadth-first search (BFS). In some embodiments, the tree traversal technique can comprise a depth-first search (DFS). In some embodiments, the tree traversal technique can comprise a breadth-first search (BFS).

In some embodiments, (c) can comprise applying a hash algorithm to the plurality of files of the assessment of the eCOA. In some embodiments, the hash algorithm can be a deterministic algorithm. In some embodiments, the hash algorithm can be a deterministic algorithm based on an order in which the plurality of files of the assessment of the eCOA is hashed. In some embodiments, the hash algorithm can be a message authentication code (MAC) algorithm. In some embodiments, the MAC algorithm can be a Keyed-Hash MAC (HMAC) algorithm. In some embodiments, the hash algorithm can be selected from Message Digest 5 (MD5), Secure Hash Algorithm (SHA)-0, Secure Hash Algorithm (SHA)-1, Secure Hash Algorithm (SHA)-2, Secure Hash Algorithm (SHA)-224, Secure Hash Algorithm (SHA)-256, Secure Hash Algorithm (SHA)-384, Secure Hash Algorithm (SHA)-512, Microsoft LAN Manager (LANMAN), Microsoft NT LAN Manager (NTLM), NTLMv2 or a combination thereof.

In some embodiments, (a) can comprise retrieving the assessment of the eCOA from a database. In some embodiments, the method further can comprise retrieving the assessment of the eCOA from the database over a computer network. In some embodiments, the computer network can be a cloud-based network.

In some embodiments, the method further can comprise, prior to (a), generating the assessment by performing the first validation of the eCOA. In some embodiments, the method further can comprise storing the assessment in a database. In some embodiments, the method further can comprise, prior to (b), generating the first hash value by hashing the plurality of files of the assessment of the eCOA. In some embodiments, the method further can comprise storing the first hash value in a database. In some embodiments, the first validation of the eCOA can be performed by regression testing.

In some embodiments, the method further can comprise generating an indication that the eCOA has been validated. In some embodiments, the method further can comprise providing the indication that the eCOA has been validated to a user. In some embodiments, the method further can comprise, responsive to the indication that the eCOA has been validated, using the eCOA without performing further validation of the eCOA. In some embodiments, the method further can comprise, responsive to the indication that the eCOA has been validated, using the eCOA without performing further development of the eCOA. In some embodiments, the method further can comprise using the eCOA to construct a clinical trial.

In some embodiments, the method further can comprise generating an indication that the eCOA is not valid when the second hash value is not equal to the first hash value. In some embodiments, the method further can comprise providing the indication that the eCOA is not valid to a user. In some embodiments, the method further can comprise, responsive to the indication that the eCOA is not valid, obtaining a second assessment of the eCOA by performing a second validation of the eCOA. In some embodiments, the method further can comprise, responsive to the indication that the eCOA is not valid, obtaining a second eCOA and validating the second eCOA. In some embodiments, validating the second eCOA can comprise: obtaining a second assessment of the second eCOA, the second assessment comprising a second plurality of files generated by performing a second validation of the second eCOA; obtaining a third hash value associated with the second assessment of the second eCOA, the third hash value generated by hashing a second plurality of files of the second assessment of the second eCOA; hashing the second plurality of files of the second assessment of the second eCOA to generate a fourth hash value; and validating the second eCOA when the fourth hash value is equal to the third hash value. In some embodiments, the method further can comprise permitting use of the eCOA only upon validation of the eCOA when the second hash value is equal to the first hash value.

In another aspect, the present disclosure can provide for a computer system for validation of an electronic clinical trial outcome assessment (eCOA), comprising: a database that is configured to store (i) an assessment of an eCOA, the assessment comprising a plurality of files generated by performing a first validation of the eCOA and (ii) a first hash value associated with the assessment of the eCOA, the first hash value generated by hashing the plurality of files of the assessment of the eCOA; and one or more computer processors operatively coupled to the database, wherein the one or more computer processors can be individually or collectively programmed to: hash the plurality of files of the assessment of the eCOA to generate a second hash value; and validate the eCOA when the second hash value is equal to the first hash value.

In some embodiments, hashing the plurality of files of the assessment of the eCOA can comprise sequentially hashing the plurality of files of the assessment of the eCOA. In some embodiments, hashing the plurality of files of the assessment of the eCOA can comprise hashing the plurality of files of the assessment of the eCOA in a pre-determined order. In some embodiments, the plurality of files can comprise one or more folders. In some embodiments, the pre-determined order corresponds to a tree traversal technique. In some embodiments, the tree traversal technique can comprise a depth-first search (DFS) or a breadth-first search (BFS). In some embodiments, the tree traversal technique can comprise a depth-first search (DFS). In some embodiments, wherein the tree traversal technique can comprise a breadth-first search (BFS).

In some embodiments, hashing the plurality of files of the assessment of the eCOA can comprise applying a hash algorithm to the plurality of files of the assessment of the eCOA. In some embodiments, the hash algorithm can be a deterministic algorithm. In some embodiments, the hash algorithm can be a deterministic algorithm based on an order in which the plurality of files of the assessment of the eCOA is hashed. In some embodiments, the hash algorithm can be a message authentication code (MAC) algorithm. In some embodiments, the MAC algorithm can be a Keyed-Hash MAC (HMAC) algorithm. In some embodiments, the hash algorithm ca be selected from Message Digest 5 (MD5), Secure Hash Algorithm (SHA)-0, Secure Hash Algorithm (SHA)-1, Secure Hash Algorithm (SHA)-2, Secure Hash Algorithm (SHA)-224, Secure Hash Algorithm (SHA)-256, Secure Hash Algorithm (SHA)-384, Secure Hash Algorithm (SHA)-512, Microsoft LAN Manager (LANMAN), Microsoft NT LAN Manager (NTLM), NTLMv2 or a combination thereof.

In some embodiments, the one or more computer processors can be individually or collectively programmed to further retrieve the assessment of the eCOA from a second database. In some embodiments, the one or more computer processors can be individually or collectively programmed to further retrieve the assessment of the eCOA from the second database over a computer network. In some embodiments, the computer network can be a cloud-based network.

In some embodiments, the one or more computer processors can be individually or collectively programmed to further, prior to (a), generate the assessment by performing the first validation of the eCOA. In some embodiments, the one or more computer processors can be individually or collectively programmed to further store the assessment in a database. In some embodiments, the one or more computer processors can be individually or collectively programmed to further, prior to (b), generate the first hash value by hashing the plurality of files of the assessment of the eCOA. In some embodiments, the one or more computer processors can be individually or collectively programmed to further store the first hash value in a database. In some embodiments, the first validation of the eCOA is performed by regression testing.

In some embodiments, the one or more computer processors can be individually or collectively programmed to further generate an indication that the eCOA has been validated. In some embodiments, the one or more computer processors can be individually or collectively programmed to further provide the indication that the eCOA has been validated to a user. In some embodiments, the one or more computer processors can be individually or collectively programmed to further, responsive to the indication that the eCOA has been validated, use the eCOA without performing further validation of the eCOA. In some embodiments, the one or more computer processors can be individually or collectively programmed to further, responsive to the indication that the eCOA has been validated, use the eCOA without performing further development of the eCOA. In some embodiments, the one or more computer processors can be individually or collectively programmed to further use the eCOA to construct a clinical trial.

In some embodiments, the one or more computer processors can be individually or collectively programmed to further generate an indication that the eCOA is not valid when the second hash value is not equal to the first hash value. In some embodiments, the one or more computer processors can be individually or collectively programmed to further provide the indication that the eCOA is not valid to a user. In some embodiments, the one or more computer processors can be individually or collectively programmed to further, responsive to the indication that the eCOA is not valid, obtain a second assessment of the eCOA by performing a second validation of the eCOA. In some embodiments, the one or more computer processors can be individually or collectively programmed to further, responsive to the indication that the eCOA is not valid, obtain a second eCOA and validating the second eCOA. In some embodiments, validating the second eCOA can comprise: obtaining a second assessment of the second eCOA, the second assessment comprising a second plurality of files generated by performing a second validation of the second eCOA; obtaining a third hash value associated with the second assessment of the second eCOA, the third hash value generated by hashing a second plurality of files of the second assessment of the second eCOA; hashing the second plurality of files of the second assessment of the second eCOA to generate a fourth hash value; and validating the second eCOA when the fourth hash value is equal to the third hash value. In some embodiments, the one or more computer processors can be individually or collectively programmed to further permit use of the eCOA only upon validation of the eCOA when the second hash value is equal to the first hash value.

In another aspect, the present disclosure can provide for a non-transitory computer-readable medium comprising machine-executable instructions which, upon execution by one or more computer processors, perform a method for validation of an electronic clinical trial outcome assessment (eCOA), the method comprising: (a) obtaining an assessment of an eCOA, the assessment comprising a plurality of files generated by performing a first validation of the eCOA; (b) obtaining a first hash value associated with the assessment of the eCOA, the first hash value generated by hashing the plurality of files of the assessment of the eCOA; (c) hashing the plurality of files of the assessment of the eCOA to generate a second hash value; and (d) validating the eCOA when the second hash value is equal to the first hash value.

In some embodiments, (c) can comprise sequentially hashing the plurality of files of the assessment of the eCOA. In some embodiments, (c) can comprise hashing the plurality of files of the assessment of the eCOA in a pre-determined order. In some embodiments, the plurality of files can comprise one or more folders. In some embodiments, the pre-determined order corresponds to a tree traversal technique. In some embodiments, the tree traversal technique can comprise a depth-first search (DFS) or a breadth-first search (BFS). In some embodiments, the tree traversal technique can comprise a depth-first search (DFS). In some embodiments, the tree traversal technique can comprise a breadth-first search (BFS).

In some embodiments, (c) can comprise applying a hash algorithm to the plurality of files of the assessment of the eCOA. In some embodiments, the hash algorithm can be a deterministic algorithm. In some embodiments, the hash algorithm can be a deterministic algorithm based on an order in which the plurality of files of the assessment of the eCOA is hashed. In some embodiments, the hash algorithm can be a message authentication code (MAC) algorithm. In some embodiments, the MAC algorithm can be a Keyed-Hash MAC (HMAC) algorithm. In some embodiments, the hash algorithm can be selected from Message Digest 5 (MD5), Secure Hash Algorithm (SHA)-0, Secure Hash Algorithm (SHA)-1, Secure Hash Algorithm (SHA)-2, Secure Hash Algorithm (SHA)-224, Secure Hash Algorithm (SHA)-256, Secure Hash Algorithm (SHA)-384, Secure Hash Algorithm (SHA)-512, Microsoft LAN Manager (LANMAN), Microsoft NT LAN Manager (NTLM), NTLMv2 or a combination thereof.

In some embodiments, (a) can comprise retrieving the assessment of the eCOA from a database. In some embodiments, the method further can comprise retrieving the assessment of the eCOA from the database over a computer network. In some embodiments, the computer network can be a cloud-based network.

In some embodiments, the method further can comprise, prior to (a), generating the assessment by performing the first validation of the eCOA. In some embodiments, the method further can comprise storing the assessment in a database. In some embodiments, the method further can comprise, prior to (b), generating the first hash value by hashing the plurality of files of the assessment of the eCOA. In some embodiments, the method further can comprise storing the first hash value in a database. In some embodiments, the first validation of the eCOA can be performed by regression testing.

In some embodiments, the method further can comprise generating an indication that the eCOA has been validated. In some embodiments, the method further can comprise providing the indication that the eCOA has been validated to a user. In some embodiments, the method further can comprise, responsive to the indication that the eCOA has been validated, using the eCOA without performing further validation of the eCOA. In some embodiments, the method further can comprise, responsive to the indication that the eCOA has been validated, using the eCOA without performing further development of the eCOA. In some embodiments, the method further can comprise using the eCOA to construct a clinical trial.

In some embodiments, the method further can comprise generating an indication that the eCOA is not valid when the second hash value is not equal to the first hash value. In some embodiments, the method further can comprise providing the indication that the eCOA is not valid to a user. In some embodiments, the method further can comprise, responsive to the indication that the eCOA is not valid, obtaining a second assessment of the eCOA by performing a second validation of the eCOA. In some embodiments, the method further can comprise, responsive to the indication that the eCOA is not valid, obtaining a second eCOA and validating the second eCOA. In some embodiments, validating the second eCOA can comprise: obtaining a second assessment of the second eCOA, the second assessment comprising a second plurality of files generated by performing a second validation of the second eCOA; obtaining a third hash value associated with the second assessment of the second eCOA, the third hash value generated by hashing a second plurality of files of the second assessment of the second eCOA; hashing the second plurality of files of the second assessment of the second eCOA to generate a fourth hash value; and validating the second eCOA when the fourth hash value is equal to the third hash value. In some embodiments, the method further can comprise permitting use of the eCOA only upon validation of the eCOA when the second hash value is equal to the first hash value.

Another aspect of the present disclosure can provide for a non-transitory computer-readable medium comprising machine executable code that, upon execution by one or more computer processors, implements any of the methods above or elsewhere herein.

Another aspect of the present disclosure can provide for a system comprising one or more computer processors and computer memory coupled thereto. The computer memory can comprise machine executable code that, upon execution by the one or more computer processors, implements any of the methods above or elsewhere herein.

FIG. 1 shows an example of a method 100 for validation of an electronic clinical trial outcome assessment (eCOA), in accordance with disclosed embodiments. The method may comprise obtaining an assessment (e.g., a standardized assessment) of an eCOA comprising a plurality of files generated by performing a first validation of the eCOA, as in operation 102. For example, the assessment may be obtained from a database, a repository, or a versioning system. Next, the method may comprise obtaining a first hash value associated with the assessment of the eCOA, generated by hashing the plurality of files of the assessment of the eCOA (as in operation 104). For example, the first hash value may be obtained from a database, a repository, or a versioning system. Next, the method may comprise hashing the plurality of files of the assessment (e.g., the standard assessment which was retrieved from the database, repository, or versioning system) of the eCOA to generate a second hash value (as in operation 106). For example, the second hash value may be generated using the same hash algorithm as that used to generate the first hash value (e.g., which was retrieved from the database, repository, or versioning system). For example, the second hash value may be generated by hashing the plurality of files of the assessment in the same order as that used to generate the first hash value (e.g., which was retrieved from the database, repository, or versioning system). Next, the method may comprise validating the eCOA when the second hash value is equal to the first hash value (as in operation 108). For example, operations 106 and 108 can be performed during client study for the standardized assessment (e.g., which was retrieved from the database, repository, or versioning system for re-use).

In some embodiments, an assessment (e.g., eCOA assessment) can be built (e.g., following Standard Operating Procedures and best software development practices). The built software may comprise a folder that contains all the files and subfolders that make up the eCOA assessment, from the point the assessment was started to the point the assessment was finished. This folder may be copied into any eCOA project, and the eCOA assessment may then be displayed to the user and be run as developed.

When the assessment finishes validation, the content of the assessment may be hashed to generate a hash value, and the hash value may be stored for future retrieval and comparison. The hashing algorithm can comprise traversing the folders, processing the files in the folder in a specific order (e.g., sequence of files), storing the content of the files, and hashing the content of the files. This procedure may be ordered and deterministic, which means that every time the hashing algorithm is performed on a set of folders, the hashing algorithm traverses the folders and files therein in the same ordered fashion. The hashing algorithm can ensure that the same hash value is generated if the same (e.g., unchanged and unaltered) input is given. This approach implies that if no content inside any files of the library folder is changed or altered, then the generated hash value remains the same.

Using this approach, an algorithmic repeatable and deterministic method can be performed to take an assessment from a pre-built library, validate the assessment, and using the assessment while skipping redevelopment and retesting of the assessment upon validation of the assessment. Upon hashing the reused library assessment to generate a hash value, and determining that the hash value is the same as that previously generated at the time that full regression testing of the assessment was performed, the assessment is validated as being indicative of no changes being made to the contents of the library diary; therefore, the same software as before can be re-used. This technique may be used to distribute the library folder to any machine-building the clinical trial, and as long as the contents of the library folder do not change, the same hash value is produced.

In an aspect, the present disclosure can provide for a computer system for validation of an eCOA. The system can be a computer-implemented system for use or data exchange among different digital users and/or entities. In such a system, there can be a network interface that can be in network communication with digital computers of different users. The network interface may include a portal or a platform as disclosed herein. Through the network interface, a user or entity can obtain eCOA assessments and hash values associated with the eCOA assessments. The eCOA assessments can comprise a plurality of files generated by performing a first validation of the eCOA. The hash values can be generated by hashing the plurality of files of the assessment of the eCOA. The system can be configured to hash the plurality of files of the assessment of the eCOA to generate a second hash value, and to validate the eCOA when the second hash value is equal to the received hash value. Subsequent to the eCOA validation, the eCOA can then be used in a clinical trial. For example, the system can then grant access to the eCOA to the user or entity, either by the platform or by the second user or entity who receives the request, to permit the user to access at least a subset of the eCOA. Granting data access may include transferring at least a subset of the eCOA to the computer of the user. The eCOA can be stored in the cloud-based computer system, and granting data access may include (i) permitting the user to access the at least the subset of the eCOA in the cloud-based computer system or (ii) transferring the at least the subset of the eCOA from the cloud-based computer system to the computer of the user.

The system can provide features such as privacy and consent, single sign-on (SSO), data transfer, and security and trust functionalities to the user via the computer network of the system. For example, the system can enable the user to use one account (e.g., a single sign-on or SSO). As another example, the system can enable the user to transfer or delete the eCOA data. As another example, the system can provide a portal for the user to view the eCOA data, or to grant or revoke access to the eCOA data.

The systems and methods provided herein can include a user portal and/or a user platform. The portal and/or platform may be part of the network interface. The portal or platform can be used to control connection to the users and/or entities. The portal and/or platform may include a server that includes a digital processing device or a processor that can execute machine code, such as a computer program or algorithm, to enable one or more method steps or operations, as disclosed herein. Such computer programs or algorithms can be run automatically or on-demand based on one or more inputs from the users and/or entities to enable at least partly the validation, access, or transfer of eCOA data.

The portal and/or platform may comprise an application program interface (API), and may feature a patient portal (for users to view and manage eCOA data), an administrator portal (for administrators to view and manage eCOA data), a physician portal (for physicians to view and manage eCOA data), database services (e.g., for communication with telemedicine providers, interfacing with electronic health records at clinics, or interpretation and reporting), a user-facing mobile application, or any combination thereof. The portal and/or platform may offer web application and development libraries, mobile application and development libraries, a custom user interface (UI) designed to fit individual users' needs, and integration with networks (e.g., laboratory networks, physician networks, or clinical trial networks).

In some embodiments, the portal and/or platform may comprise a module configured to allow a user to design and conduct clinical trials. For example, the module can be used as a clinical trial infrastructure that is optimized for activation and accrual (e.g., enrollment of new subjects). The clinical trial infrastructure may facilitate aspects of clinical trial enrollment and operations, such as candidate matching and enrollment, and analysis and updating of patient cohorts and databases.

The portal and/or platform may include a user interface, e.g., graphical user interface (GUI). The portal and/or platform may include a web application or mobile application. The portal and/or platform may include a digital display to display information to the user and/or an input device that can interact with the user to accept input from the user.

Systems and methods of the present disclosure may differentiate stored data into multiple groups of data, each group having different privacy or security attributes used to control the access, distribution, or dissemination of data associated with that group. Any selected subset of data associated with a group, including all data associated with a group, may be anonymized in a manner that prevents the identification of an individual (e.g., a patient) from the anonymized data. For example, this anonymization can be performed by suppressing or removing fields of information within data records that have been flagged as providing personally identifiable information. As another example, the anonymization may be performed by encryption of fields, such as by using a symmetric key encryption algorithm or one key of a public/private key pair, or by application of a secure cryptographic hash such as the MD5 hash algorithm to the data and using the computed hash value in place of personally identifiable information from one or more fields of a data record in subsequent operations. For example, fields of information that are suppressed or removed may be recoverable only by using other fields to uniquely identify the data record in the stored data.

When encryption is used, for example, a user may recover the suppressed information if the symmetric encryption key or the other half of the public/private key pair is known by that entity. When a secure cryptographic hash is used, for example, and if the hash values have been uniquely associated with the data record, knowledge of this association may allow access to the data record personally identifiable information by an entity that has access to the original stored data.

Anonymization may be performed on demand, or on an as-needed basis in response to a request for information, or it may be performed as data are received for storage by the system. One or more symmetric or public/private encryption keys may be used to control the anonymization process. In this case, additional encryption keys may be used to either distribute anonymized data to a user that requests it by re-encrypting the data or distribute encryption key information in an encrypted form.

In some embodiments, block chain may be used with tagging, where, for instance, if an eCOA is hashed, tags may be stored for that eCOA, such as to classify an eCOA as confidential or as valid or invalid. This may be applied to an application for referencing a given eCOA to check with the database to see how it is treated.

In some embodiments, systems and methods of the present disclosure may have applications in and be deployed in environments and systems related to clinical trial management, safe eCOA exchange, and collaboration. For instance, a clinical trial management facility may be provided, where specialized documentation management control for clinical trials may be enabled in a secure collaborative environment, such as to safeguard critical information, reduce costs, and streamline operations, as well as for secure transfer and exchange of information (e.g., inside and outside of the network and firewall of a particular user). Further, the use of functionally integrated user interfaces with existing user applications may promote adoption of new site users that have traditionally employed paper-based documents in clinical studies, as well as help maintain existing site users, where administrative burdens placed on sites due to a paper-based process may cause a high turnover of investigators.

The clinical trial management facility may provide a convenient, secure way to manage critical information during clinical trials, such as in support of bringing new drugs and therapies to market. Automated workflows may be used help to move critical documents (e.g., eCOAs) from one phase to the next, easing the flow of information between organizations and saving time. In addition, audit and reporting capabilities may be provided to support transparency and compliance, which leads to faster approvals by regulatory agencies.

In some embodiments, authorization information may be transmitted between parts of a distributed system, thereby allowing the information to transit untrusted systems while still preserving the security to ensure that the authorization is not tampered with. In some embodiments, data being transferred or stored may be cryptographically signed for both authentication of origin and tamper detection. For instance, a message authentication code (MAC), a keyed-hash MAC (HMAC), and the like may be used in the process. As used herein, MAC generally refers to a short piece of information used to authenticate a message and to provide integrity and authenticity assurances on the message. As used herein, an HMAC generally refers to a keyed-hash type of MAC that is a specific construction for calculating a MAC involving a cryptographic hash function in combination with a secret cryptographic key. In some embodiments, a progressive HMAC processor may be used, such that an HMAC can be computed by processing piecewise chunks or a stream, rather than a complete, contiguous buffer.

Systems and methods of the present disclosure may comprise Patient Reported Outcomes (PRO) and/or clinical outcome assessment (COA) validation approaches to demonstrate the clinical efficacy of a medical treatment or procedure. These forms of validation, which may be performed electronically (e.g., for an eCOA), to clinically validated outcome tools, which may be used to accumulate accurate and dependable patient endpoint data.

Electronic approaches to validation of clinical research may be performed to avoid challenges in collecting patient endpoint data using paper-based approaches, which can be archaic and inefficient. In paper-based approaches, patients may be required to complete a questionnaire or consent to an interview with a member of clinical staff, who then manually transcribe the data for processing. Common questions posed in these situations may concern the patient's general health and any specific symptoms or impairments they may have experienced. This manual, paper-based process may be inefficient and represent a drain on resources. As such, these methods of data collection may be cost- and time-inefficient, and, in some cases, unreliable.

Applying technology to leverage the sophistication of mobile devices, and their familiarity to patients to the science of clinical research, validated clinical research can be performed such that time and resources are utilized more efficiently, especially in such cases where the mobile device can have internet or WiFi connectivity. Since mobile technologies are becoming increasingly integral to people's everyday lives, they may enable ease of accessibility, cost- and time-efficiency, thereby playing an ever-increasing role in the accumulation of patient endpoint data.

Validating a COA may comprise ensuring efficiency. For example, the efficacy of delivering a validated PRO/COA instrument or questionnaire can be compared between traditional pencil-and-paper and mobile device formats, in order to assess the efficiency of these approaches. The mobile device formatted questionnaires, which may involve smartphone and/or tablets, may be developed under the supervision of the instrument or questionnaire owner. Once in place, the technology may be presented to a statistically significant user sample drawn from an appropriate research cohort of patients. This may be performed by using a crossover design, where the patients' responses are compared after they complete one of the modalities (either paper or electronic) and then complete the other modality after an allotted period of time. Each respondent may be asked a number of usability questions once they have completed the process. Responses to these questions may be vital in gauging the efficiency and accessibility of each format, and may inform a strategy moving forward.

Further, validating a COA may comprise testing for equivalency. For example, International Society of Pharmacoeconomics and Outcomes Research (ISPOR) guidelines may be used for determining equivalence between the different modalities to collecting patient data. As per the guidelines' suggestion, the level of equivalence testing may vary based on how significantly the instrument or questionnaire has been modified. Minor changes when migrating an instrument or questionnaire to an electronic format may only require cognitive debriefing for patients and usability testing. Moderate changes such as changing instruction from 'please tick' to 'please tap' when moving from paper to electronic, or changing the delivery media (for example from audio to visual), which may require equivalency testing. To assist this, randomized crossover designs may be employed, in which users are randomly assigned to either paper or electronic for their first administration, and then switched to the other format for the second. Another approach may involve randomized parallel group designs, with users in one group of the study randomly assigned to the paper format, and those in the second arm assigned to electronic. Finally, in the case of major changes being needed, the electronic version may be evaluated as if it were an entirely new instrument.

By following the above guidance, mobile ePRO or eCOA can be easily validated to become a standard tool for clinical data capture.

Computer Systems

Figure 2:
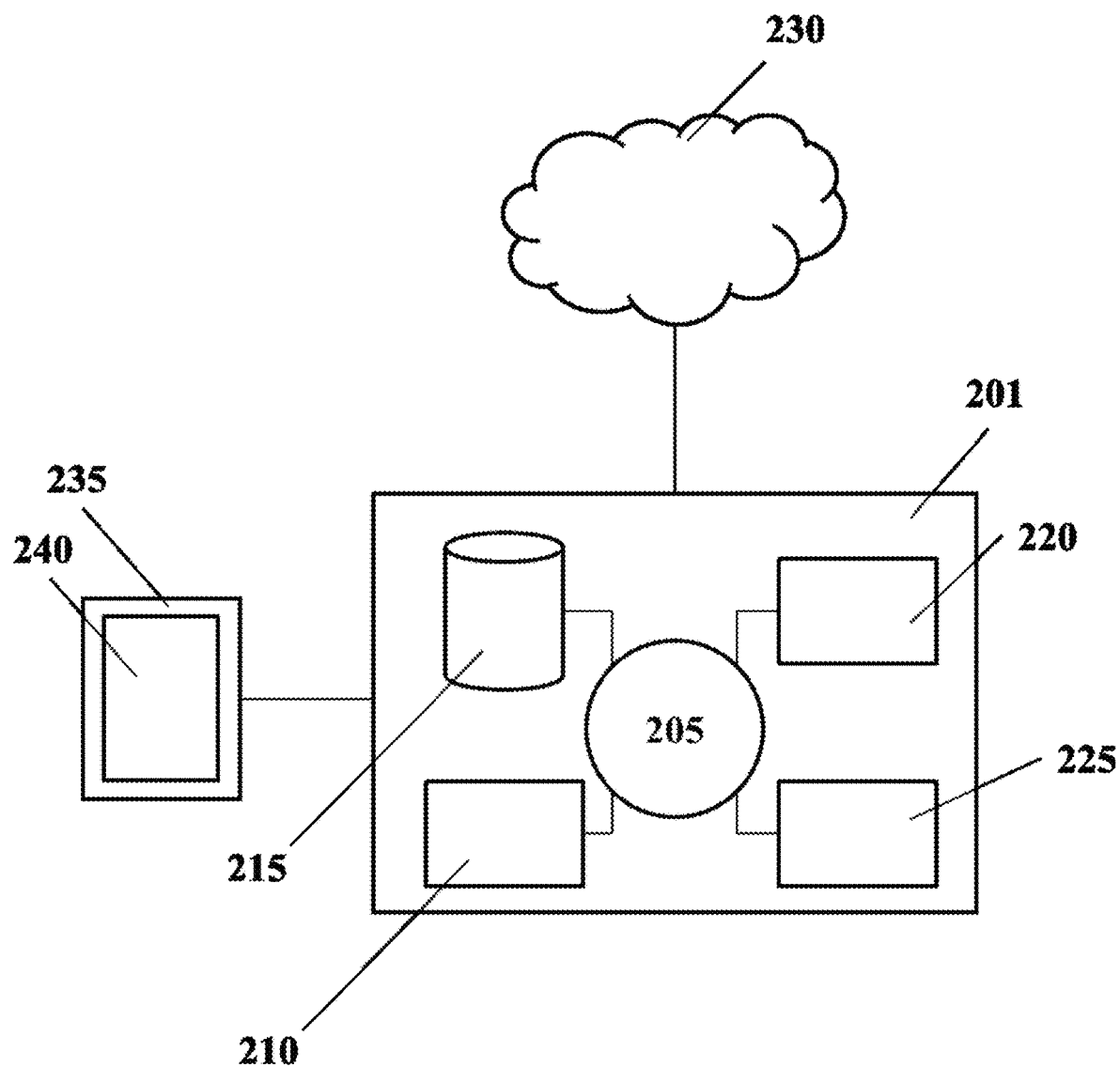
FIG. 2 shows a computer system that is programmed or otherwise configured to implement methods provided herein.

The present disclosure can provide for computer systems that are programmed to implement methods of the disclosure. FIG. 2 shows an example of a computer system 201 that is programmed or otherwise configured to perform one or more functions or operations for validating an electronic clinical trial outcome assessment (eCOA). The computer system 201 can regulate various aspects of the portal and/or platform of the present disclosure, such as, for example, obtaining an assessment of an eCOA, obtaining a hash value associated with an assessment of an eCOA, hashing files of an assessment of an eCOA to generate a hash value, and validating an eCOA based on its hash value. The computer system 201 can be an electronic device of a user or a computer system that is remotely located with respect to the electronic device. The electronic device can be a mobile electronic device.

The computer system 201 includes a central processing unit (CPU, also "processor" and "computer processor" herein) 205, which can be a single core or multi core processor, or a plurality of processors for parallel processing. The computer system 201 may also include memory or memory location 210 (e.g., random-access memory, read-only memory, flash memory), electronic storage unit 215 (e.g., hard disk), communication interface 220 (e.g., network adapter) for communicating with one or more other systems, and peripheral devices 225, such as cache, other memory, data storage and/or electronic display adapters. The memory 210, storage unit 215, interface 220 and peripheral devices 225 may be in communication with the CPU 205 through a communication bus (solid lines), such as a motherboard. The storage unit 215 can be a data storage unit (or data repository) for storing data. The computer system 201 can be operatively coupled to a computer network ("network") 230 with the aid of the communication interface 220. The network 230 can be the Internet, an internet and/or extranet, or an intranet and/or extranet that is in communication with the Internet.

The network 230 in some cases can be a telecommunication and/or data network. The network 230 can include one or more computer servers, which can enable distributed computing, such as cloud computing. For example, one or more computer servers may enable cloud computing over the network 230 ("the cloud") to perform various aspects of analysis, calculation, and generation of the present disclosure, such as, for example, obtaining an assessment of an eCOA, obtaining a hash value associated with an assessment of an eCOA, hashing files of an assessment of an eCOA to generate a hash value, and validating an eCOA based on its hash value. Such cloud computing may be provided by cloud computing platforms such as, for example, Amazon Web Services (AWS), Microsoft Azure, Google Cloud Platform, and IBM cloud. The network 230, in some cases with the aid of the computer system 201, can implement a peer-to-peer network, which may enable devices coupled to the computer system 201 to behave as a client or a server.

The CPU 205 can execute a sequence of machine-readable instructions, which can be embodied in a program or software. The instructions may be stored in a memory location, such as the memory 210. The instructions can be directed to the CPU 205, which can subsequently program or otherwise configure the CPU 205 to implement methods of the present disclosure. Examples of operations performed by the CPU 205 can include fetch, decode, execute, and writeback.

The CPU 205 can be part of a circuit, such as an integrated circuit. One or more other components of the system 201 can be included in the circuit. In some cases, the circuit can be an application specific integrated circuit (ASIC). The storage unit 215 can store files, such as drivers, libraries and saved programs. The storage unit 215 can store user data, e.g., user preferences and user programs. The computer system 201 in some cases can include one or more additional data storage units that are external to the computer system 201, such as located on a remote server that is in communication with the computer system 201 through an intranet or the Internet.

The computer system 201 can communicate with one or more remote computer systems through the network 230. For instance, the computer system 201 can communicate with a remote computer system of a user (e.g., a mobile device of the user). Examples of remote computer systems include personal computers (e.g., portable PC), slate or tablet PC's (e.g., Apple® iPad, Samsung® Galaxy Tab), telephones, Smart phones (e.g., Apple® iphone, Android-enabled device, Blackberry®), or personal digital assistants. The user can access the computer system 201 via the network 230.

Methods provided herein can be implemented by way of machine (e.g., computer processor) executable code stored on an electronic storage location of the computer system 201, such as, for example, on the memory 210 or electronic storage unit 215. The machine executable or machine-readable code can be provided in the form of software. During use, the code can be executed by the processor 205. In some cases, the code can be retrieved from the storage unit 215 and stored on the memory 210 for ready access by the processor 205. In some situations, the electronic storage unit 215 can be precluded, and machine-executable instructions are stored on memory 210.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 201, can be embodied in programming. Various aspects of the technology may be thought of as "products" or "articles of manufacture" typically in the form of machine (or processor) executable code and/or associated data that is carried on or embodied in a type of machine-readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine-readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer-readable media may be involved in carrying one or more sequences of one or more instructions to a processor for execution.

The computer system 201 can include or be in communication with an electronic display 235 that can comprise a user interface (UI) 240 for providing, for example, indications that an eCOA has been validated or indications that an eCOA is not valid. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 205. The algorithm can, for example, obtain an assessment of an eCOA, obtain a hash value associated with an assessment of an eCOA, hash files of an assessment of an eCOA to generate a hash value, and validate an eCOA based on its hash value.

EXAMPLES

Example 1: Code Structure of Hashing Algorithm

Figure 3:
FIG. 3 shows a partial screenshot of an example list of library assessments in the code repository, in accordance with disclosed embodiments.

Using systems and methods of the present disclosure, a list of assessments was pre-built and maintained in a code repository (e.g., an assessments library). Each folder in this library contains all the necessary files to get the assessment to run in a product. These folders are always prefixed with the 'Lib_'. This provides an indication that the folder is to be processed by the hashing algorithm, which is only run on items that are prefixed with 'Lib_'. FIG. 3 shows a partial screenshot of an example list of library assessments in the code repository, in accordance with disclosed embodiments.

The hashing algorithm processes the file contents of an eCOA assessment in a specific order (e.g., in a pre-determined order or sequence). If the order of the files that are processed by the hash algorithm changes, then the hashing mechanism produces a different hash value. The hashing algorithm is configured to always read a plurality of files and/or folders in the same order, regardless of the project the library folder is part of.

Figure 4:
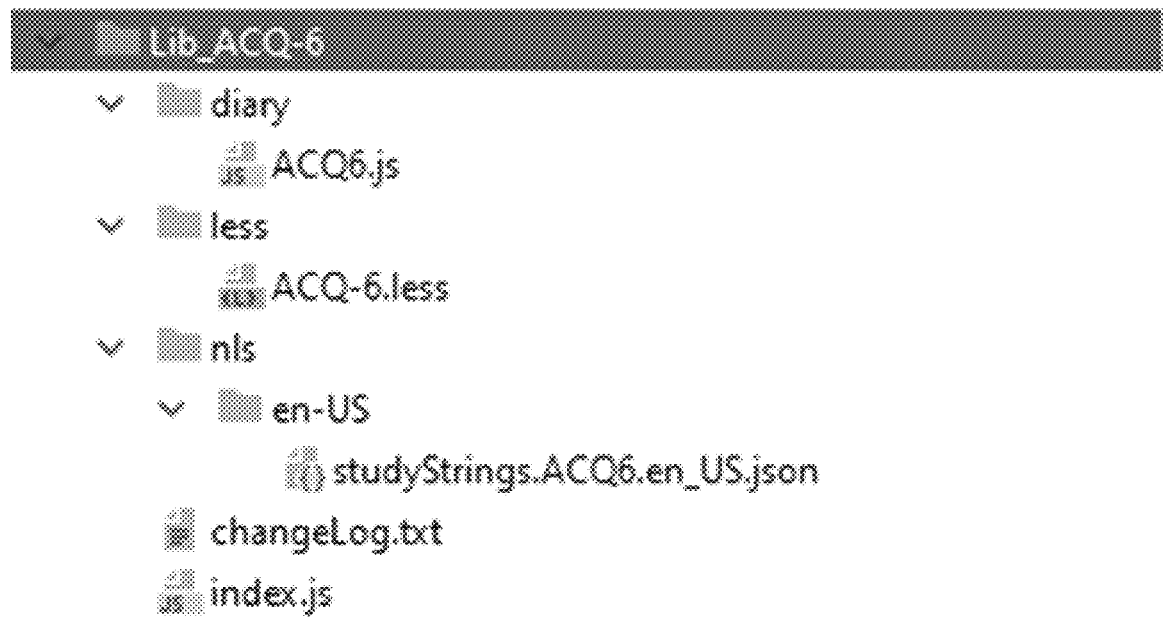
FIG. 4 shows an example of a library structure of a folder containing a library diary named ACQ-6, in accordance with disclosed embodiments.

For example, consider an example of a library diary named ACQ-6 from a folder having a library structure as shown in FIG. 4. When the hashing algorithm is run, the hashing algorithm processes the files inside Lib_ACQ-6 sequentially and in the same order. FIG. 5 shows an example of the order in which the files inside Lib_ACQ-6 are processed and their contents processed by the hashing algorithm, upon performing the hashing task, in accordance with disclosed embodiments. This hashing procedure is repeatable and deterministic in any project that Lib_ACQ-6 becomes part of. That is, the same hashing value is be produced by the hashing algorithm, if the input files and the order in which the input files are processed both remain unchanged between runs of the hashing algorithm.

Example 2: Reuse Procedure of Hashing Algorithm

Using systems and methods of the present disclosure, library items (e.g., eCOA assessments) are validated and then potentially re-used subsequent to the validation. The reuse process for library items is a stringent process. First, the library items are copied from the library code repository and pasted into the client project (e.g., under the trial/handheld/diaries or trial/tablet/diaries folder). The copying and pasting of the library items can be done manually. Alternatively, the copying and pasting of the library items can be automated, such that the manual process is reduced during reuse. The library folder in the study is never changed so as to preserve the same hash value during the validation process. If there are any changes to the location where the library folder is copied or changes to any of the contents of the library folder, then a different hash value is produced upon running the hash algorithm on the library folder.

In some embodiments, the eCOA assessment is re-used upon validating the eCOA assessment (e.g., by generating a hash value that is identical to a previous hash value of the eCOA assessment). In some embodiments, the eCOA assessment is not re-used if the validation of the eCOA assessment indicates that the eCOA assessment is invalid (when a hash value is generated that is different from a previous hash value of the eCOA assessment).

Example 3: Testing Procedure of Hashing Algorithm

Using systems and methods of the present disclosure, a library item (e.g., an eCOA assessment) is tested. The library item is pre-built ahead of study time. After the library item is built, the library item proceeds to a pre-testing phase, where full regression testing is performed on the library item. Next, a pre-built and pre-tested library folder is incorporated into a given project, and the library folder may skip through regression testing on the device. The testing procedure is skipped upon validation of the library item (e.g., when the comparison of the hash value of the library folder in the project is found to be identical to the hash value of the library folder after pre-testing phase was completed (e.g., which was stored for later retrieval and comparison). This testing can be skipped because the identical hash values constitute proof that none of the contents (e.g., no code) of the library folder were modified since the prior validation was performed and the previous hash value was generated.

FIG. 6 shows an example of the output of the hashing algorithm, in accordance with disclosed embodiments. This output has the same format, regardless of the time or project the hashing algorithm is performed on. The output format also looks the same when the hashing algorithm is performed in the pre-testing phase. The output format includes the following key items: the date time of the hash and the assessment modality.

The date time of the hash appears in the output of the hashing algorithm. On the first line, the output indicates when the hashing algorithm was performed on the library folder. Further, the assessment modality appears in the output of the hashing algorithm. On the first line, the output indicates what product the hashing was performed for. For example, the assessment modality may be a laptop computer, a handheld computer, a tablet computer, or a smartphone. Every line of the output following that indicates the name of the library diary and then its unique hash value generated from processing the file contents of that library in the same specific order.

The hashing algorithm is performed to generate a hashing output each time a project is built for deployment on a device. The testing procedure can comprise comparing the hash value generated for a library diary in this file during a project build to the hash value generated for that library diary during the pre-testing phase. If the hash values are found to be identical, then that outcome provides an indication of algorithmic proof that no code content was modified. Therefore, the full regression testing on that diary may be skipped based on the validation of the library diary.

While preferred embodiments have been shown and described herein, it will be obvious to those skilled in the art that such embodiments are provided by way of example only. It is not intended that the disclosure be limited by the specific examples provided within the specification. The descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A computer-implemented method for transmitting an assessment of an electronic clinical trial outcome assessment (eCOA) software to a user, comprising:
   (a) accessing, by an interface of a mobile platform, a database to obtain plural pre-built library folders from the database, wherein each library folder comprises one or more files, wherein each library folder has an associated hash value;
   (b) compiling, by the interface, the plural pre-built library folders into a project to be deployed on the mobile platform;
   (c) generating, by the interface for each library folder of plural library folders of an eCOA, a first hash value by applying a hashing algorithm to the one or more files of a respective library folder of the project in a specified order;
   (d) generating, by the interface, a second hash value by applying a hashing algorithm to the plural folders of an eCOA assessment including the one or more files of each library folder;
   (e) storing, by the interface, the first hash value and the second hash value in memory of the mobile platform;
   (e) comparing, by the interface:
      the first hash value of each library folder of the project to be deployed on the mobile platform to a pre-build first hash value of the library folder that was generated prior to the project being deployed to the mobile platform; and
      the second hash value to a standardized hash value of the eCOA that was generated prior to the project being deployed to the mobile platform;
   (f) analyzing, by the interface, features of the electronically formatted to determine a significance of changes between the eCOA and a non-electronic clinical outcome assessment stored in memory;
   (g) validating, by the interface, the plural files of the eCOA, when the first hash value is equal to the pre-built first hash value, the second hash value is equal to the standardized hash value, and the significance of changes meets a specified threshold; and
   (h) deploying, by the interface to the mobile platform, the eCOA for use on the mobile platform.

2. The method of claim 1, wherein at least one of the first hashing algorithm and the second hashing algorithm is a deterministic algorithm.

3. The method of claim 2, wherein the deterministic algorithm is based on an order in which at least one of the first hashing algorithm and the second hashing algorithm is applied to the plurality of files of the assessment of the eCOA software.

4. The method of claim 1, wherein at least one of the first hashing algorithm and the second hashing algorithm is a message authentication code (MAC) algorithm.

5. The method of claim 1, wherein at least one of the first hashing algorithm and the second hashing algorithm is MD5.

6. The method of claim 1, further comprising:
generating an indication that the eCOA software has been validated.

7. The method of claim 1, further comprising:
generating an indication that the eCOA software is not valid, if the second hash value is not equal to the standardized hash value.

8. A mobile device for validating an electronic clinical trial outcome assessment (eCOA), the mobile device comprising:
a processor configured to execute program code for generating an application program interface, the application program interface causing the processor to:
(i) receive a request for deploying an eCOA to the mobile device;
(ii) access a database over a network to obtain plural plural pre-built library folders, each library folder including one or more files, and each library folder has an associated hash value;
(iii) compile the plural pre-built library folders into a project to be deployed on the mobile platform;
(iii) generate a first hash value for each library folder of the plural library folders of the eCOA by applying a hashing algorithm to the one or more files of a respective library folder of the project in a specified order;
(iv) generate a second hash value by applying a hashing algorithm to the plural folders of an eCOA including the one or more files of each library folder;
(v) storing, by the interface, the first hash value and the second hash value in memory of the mobile platform;
(vi) compare the first hash value of each library folder of the project to be deployed on the mobile platform to a pre-build first hash value of the library folder that was generated prior to the project being deployed to the mobile platform;
(vii) compare the second hash value to a standardized hash value of the eCOA that was generated prior to the project being deployed to the mobile platform;
(viii) analyzing, by the interface, features of the electronically formatted to determine a significance of changes between the eCOA and a non-electronic clinical outcome assessment stored in memory;
(ix) validate the plural files of the eCOA, when first hash value is equal to the pre-built first hash value, the second hash value is equal to the first standardized hash value, and the significance of the eCOA meets a specified threshold; and
(x) deploy the eCOA for to the processor on the mobile platform.

9. The mobile device of claim 8, wherein at least one of the first hashing algorithm and the second hashing algorithm is a deterministic algorithm.

10. The computer system of claim 9, wherein the deterministic algorithm is based on an order in which the hashing algorithm is applied to the plurality of files of the assessment of the eCOA software.

11. The mobile device of claim 8, wherein at least one of the first hashing algorithm the second hashing algorithm is a message authentication code (MAC) algorithm.

12. The computer system of claim 8, wherein at least one of the first hashing algorithm and the second hashing algorithm is MD5.

13. The mobile device of claim 8, wherein the further configured to generate an indication that the eCOA software is not valid, if the second hash value is not equal to the first hash value.

* * * * *